(12) United States Patent
Naito et al.

(10) Patent No.: US 8,252,237 B2
(45) Date of Patent: Aug. 28, 2012

(54) SUBSTANCE DETECTION SENSOR

(75) Inventors: Toshiki Naito, Osaka (JP); Hiroshi Yamazaki, Osaka (JP); Toshihiko Omote, Osaka (JP)

(73) Assignee: Nitto Denko Corporation, Osaka (JP)

( * ) Notice: Subject to any disclaimer, the term of this patent is extended or adjusted under 35 U.S.C. 154(b) by 89 days.

(21) Appl. No.: 12/448,853

(22) PCT Filed: Oct. 16, 2007

(86) PCT No.: PCT/JP2007/070186
§ 371 (c)(1),
(2), (4) Date: Nov. 17, 2009

(87) PCT Pub. No.: WO2008/084582
PCT Pub. Date: Jul. 17, 2008

(65) Prior Publication Data
US 2010/0072065 A1  Mar. 25, 2010

(30) Foreign Application Priority Data
Jan. 12, 2007  (JP) .................................. 2007-004558

(51) Int. Cl.
*G01N 15/06* (2006.01)
*G01N 33/00* (2006.01)
*G01N 33/48* (2006.01)

(52) U.S. Cl. ............. 422/98; 422/50; 422/68.1; 422/83; 422/82.01; 422/82.02

(58) Field of Classification Search .................... 422/50, 422/68.1, 83, 82.01, 82.02, 98
See application file for complete search history.

(56) References Cited

U.S. PATENT DOCUMENTS

| 4,988,539 A | * | 1/1991 | Breuil et al. ............... 427/126.3 |
| 5,173,684 A | | 12/1992 | Ijiri et al. |
| 5,571,401 A | | 11/1996 | Lewis et al. |
| 6,134,946 A | * | 10/2000 | Liu et al. ..................... 73/31.06 |
| 2004/0189331 A1 | * | 9/2004 | Girshovich et al. ........... 324/694 |

FOREIGN PATENT DOCUMENTS

| JP | 63-083651 | 4/1988 |
| JP | 3-96847 | 4/1991 |
| JP | 4-084749 | 3/1992 |
| JP | 5-26832 | 2/1993 |
| JP | 6-347432 | 12/1994 |
| JP | 7-12767 | 1/1995 |
| JP | 8-261969 | 10/1996 |
| JP | 10-104185 | 4/1998 |
| JP | 11-503231 | 3/1999 |
| JP | 2000-19136 | 1/2000 |
| JP | 2002-509609 | 3/2002 |
| WO | WO 99/01733 | 1/1999 |
| WO | WO 2005/047528 | 5/2005 |

* cited by examiner

*Primary Examiner* — Brian J Sines
(74) *Attorney, Agent, or Firm* — Jean C. Edwards, Esq.; Edwards Neils PLLC

(57) ABSTRACT

A substance detection sensor comprises an insulation layer (2) having flexibility, two electrodes (3A, 3B) so disposed on the insulation layer as to be opposite to each other at a space therebetween and connected to an electric resistance detector, and a conductive layer (4) which is so formed on the insulation layer as to span the two electrodes and to be electrically connected to the two electrodes. The swelling ratio of the conductive layer (4) is changed according to the type and/or the quantity of a specific substance.

6 Claims, 4 Drawing Sheets

SUBSTANCE DETECTION SENSOR

CROSS-REFERENCE TO RELATED APPLICATIONS

The present invention is a 35 USC 371 national stage entry of PCT/JP2007/070186, filed Oct. 16, 2007, which claims priority from Japanese Patent Application No. 2007-004558, filed Jan. 12, 2007, the contents of all of which are herein incorporated by reference in their entirety.

TECHNICAL FIELD

The present invention relates to a substance detection sensor, and particularly to a substance detection sensor for primarily detecting the type and quantity of a gas.

BACKGROUND ART

Conventionally, a substance sensor for detecting a gas or a liquid has been used for various industrial applications. Such a substance sensor is used in qualitative analysis and quantitative analysis of a specific gas or liquid.

For example, a chemical sensor has been proposed which includes a matrix, a resistor formed on the matrix, made of a mixture of a conductive substance and a nonconductive organic polymer, and having a chemical sensitivity, and first and second conductive leads disposed on the matrix in mutually spaced apart relation, and electrically connected via the resistor. It has been proposed to use, as the matrix in the chemical sensor, a nonconductive board made of a glass or a ceramic (see, e.g., Patent Document 1 shown below).

Patent Document 1: Domestic-Phase PCT Patent Application No. 11-503231 (FIG. 4A')

DISCLOSURE OF THE INVENTION

Problem to be Solved

On the other hand, in recent years, it has been attempted to reduce the thickness and size of equipment used for various industrial applications, or improve the functionality thereof by providing a movable portion, and it has been requested to detect a substance in a narrow small portion or the movable portion in such equipment.

However, in the chemical sensor described in Patent Document 1 mentioned above, the nonconductive board made of a glass or a ceramic is hard and rigid so that it is difficult to dispose the chemical sensor including such a nonconductive board in the narrow small portion or movable portion of the equipment.

An object of the present invention is to provide a substance detection sensor which can be easily disposed in a narrow small portion or a movable portion.

Means for Solving the Problem

To attain the object, a substance detection sensor of the present invention includes an insulating layer having flexibility, two electrodes disposed on the insulating layer in mutually spaced-apart and opposing relation, and connected to an electric resistance detector, and a conductive layer formed on the insulating layer so as to span between the two electrodes and be electrically connected thereto, the conductive layer swelling at a ratio varying in accordance with a type and/or a quantity of a specific substance.

In the substance detection sensor of the present invention, it is preferable that the substance is gas.

In the substance detection sensor of the present invention, it is preferable that the insulating layer is made of a liquid crystal polymer.

In the substance detection sensor of the present invention, it is preferable that the insulating layer is made of polyethylene terephthalate.

Preferably, the substance detection sensor of the present invention further includes a metal layer which is formed under the insulating layer.

Preferably, the substance detection sensor of the present invention further includes a tin layer or a tin alloy layer which is formed so as to cover the two electrodes.

Preferably, the substance detection sensor of the present invention further includes a gold layer which is formed so as to cover the two electrodes.

Preferably, the substance detection sensor of the present invention further includes a gold layer which is formed so as to cover the tin layer or the tin alloy layer.

Effect of the Invention

Since the substance detection sensor of the present invention includes the insulating layer having flexibility, the insulating layer can be flexibly deformed to allow the substance detection sensor to be disposed in a narrow small portion or to be disposed in a movable portion, and follow the movement thereof.

As a result, by detecting the electric resistance value of the conductive layer which swells at the ratio varying in accordance with the specific substance using an electric resistance detector, the detection of a substance in the narrow small portion or the movable portion can be reliably performed.

EMBODIMENTS OF THE INVENTION

Figure 1:
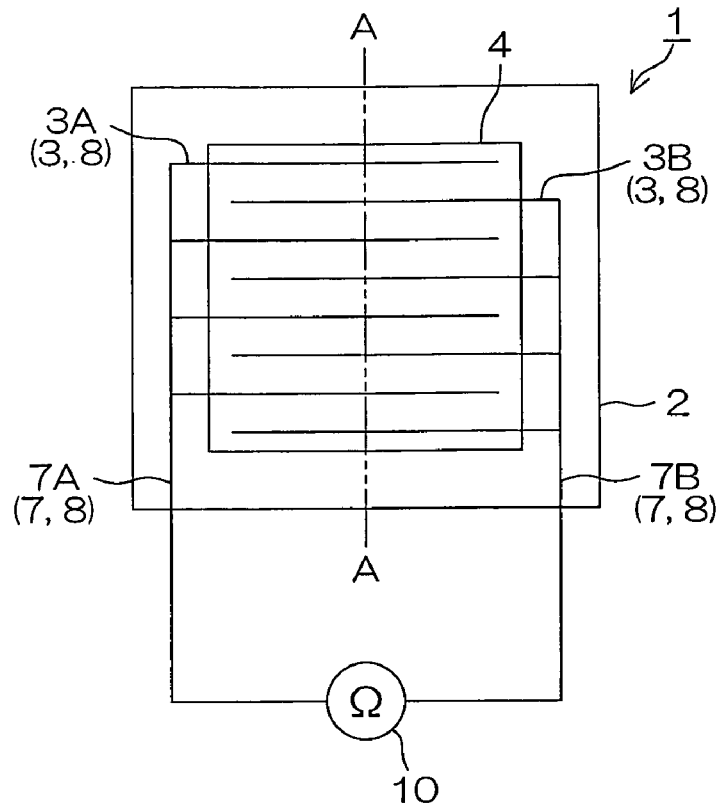
FIG. 1 is a plan view of a gas detection sensor as an embodiment of a substance detection sensor of the present invention.
Figure 2:
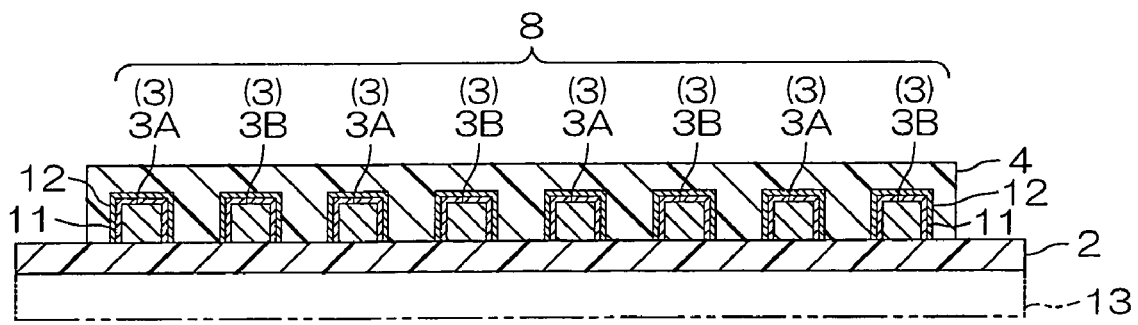
FIG. 2 is a cross-sectional view along the line A-A of the gas detection sensor shown in FIG. 1.

FIG. 1 is a plan view of a gas detection sensor as an embodiment of a substance detection sensor of the present invention. FIG. 2 is a cross-sectional view along the line A-A of the gas detection sensor shown in FIG. 1.

In FIG. 2, a gas detection sensor 1 includes an insulating layer 2, a conductive pattern 8 formed on the insulating layer 2, a first protective layer 11 formed so as to cover the conductive pattern 8, a second protective layer 12 formed so as to cover the first protective layer 11, and a conductive layer 4 formed on the insulating layer 2 so as to cover the second protective layer 12.

The insulating layer 2 has flexibility, and is formed in, e.g., a sheet (film) shape having a generally rectangular plan view shape, as shown in FIG. 1.

The conductive pattern 8 is formed as a wired circuit pattern on the insulating layer 2, and includes electrodes 3 and wires 7.

The electrodes 3 are formed so as to linearly extend between the both end surfaces of the insulating layer 22 which oppose each other, and include two types of electrodes, i.e., first electrodes 3A and second electrodes 3B.

The plurality of first electrodes 3A are arranged in parallel in a direction perpendicular to a direction in which the electrodes 3 extend. The individual first electrodes 3A are arranged in mutually spaced-apart relation in the parallel direction of the first electrodes 3A.

The plurality of second electrodes 3B are arranged in parallel in the direction perpendicular to the direction in which the electrodes 3 extend. The individual second electrodes 3B are arranged in mutually spaced-apart relation so as to be disposed between the individual first electrodes 3A in the parallel direction of the second electrodes 3B (except for the second electrode 3B at one end portion in the parallel direction).

Of the electrodes 3, the individual first electrodes 3A and the individual second electrodes 3B are alternately arranged in spaced-apart relation in the parallel direction of the first electrodes 3A and the second electrodes 3B.

The wires 7 include a first wire 7A connected to the first electrodes 3A, and a second wire 7B connected to the second electrodes 3B.

The first wire 7A is disposed on one side end portion (one side end portion in the direction in which the electrodes 3 extend, which holds true hereinafter) of the insulating layer 2, and linearly formed so as to extend along the parallel direction of the first electrodes 3A, and be connected to one side end portion of each of the first electrodes 3A. The first wire 7A electrically connects each of the first electrodes 3A and an electric resistance detector 10.

The second wire 7B is disposed on the other side end portion (the other side end portion in the direction in which the electrodes 3 extend, which holds true hereinafter) of the insulating layer 2, and linearly formed so as to extend along the parallel direction of the second electrodes 3B, and be connected to the other side end portion of each of the first electrodes 3B. The second wire 7B electrically connects each of the second electrodes 3B and the electric resistance detector 10.

In the conductive pattern 8, the first electrodes 3A and the second wires 7B are formed to be displaced from each other in one direction and in the other direction, respectively, in the direction in which the electrodes 3 extend. As a result, in the conductive pattern 8, the first electrodes 3A and the first wire 7A, and the second electrodes 3B and the second wire 7B are each formed in a comb-like shape, and arranged in an interdigitating configuration.

As shown in FIG. 2, the first protective layer 11 is formed so as to cover the conductive pattern 8. More specifically, the first protective layer 11 is formed directly on the surfaces (upper surface and side surfaces) of each of the first electrodes 3A and the second electrodes 3B and on the surfaces (upper surface and side surfaces) (not shown in FIG. 2) of each of the first wires 7A and the second wires 7B.

The second protective layer 12 is formed so as to cover the first protective layer 11 formed on the surface of the conductive pattern 8. More specifically, the second protective layer 12 is formed on the surfaces (upper surface and side surfaces) of the first protective layer 11.

As shown in FIG. 1, the conductive layer 4 is disposed at a general center of the insulating layer 2 when viewed in plan view, and formed in a generally rectangular plan view shape.

The conductive layer 4 is continuously formed so as to cover all the first electrodes 3A and the second electrodes 3B in the parallel direction of the first electrodes 3A and the second electrodes 3B. The conductive layer 4 is formed so as to expose the one side end portions of the first electrodes 3A, the first wires 7A, the other side end portions of the second electrodes 3B, and the second wires 7B.

Figure 3:
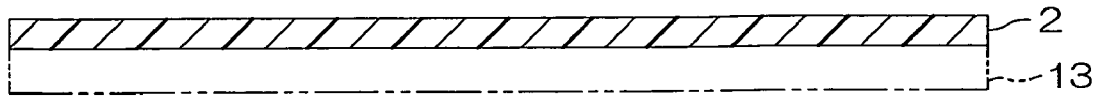
FIG. 3 is a production process view showing a producing method of the gas detection sensor shown in FIG. 2.
Figure 3:
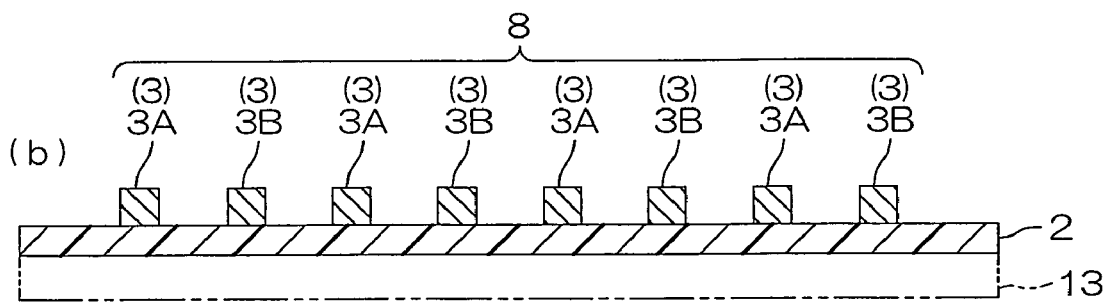
Figure 3:
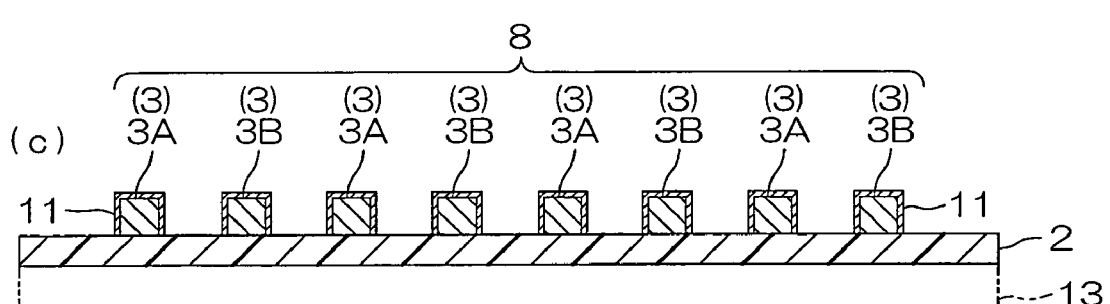
Figure 3:
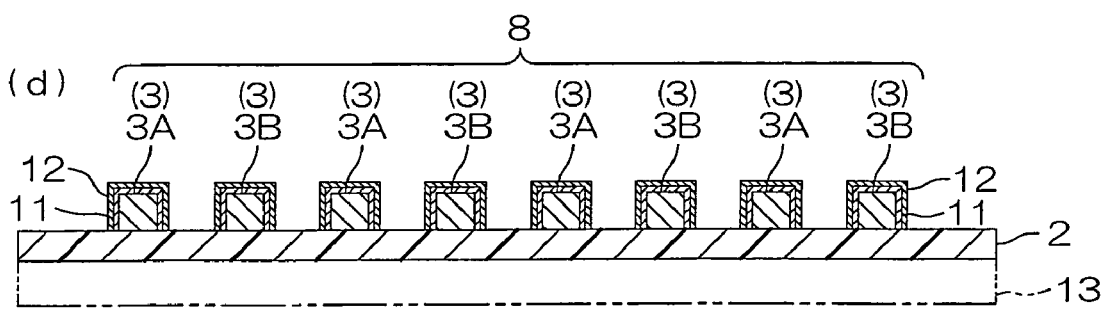
Figure 3:
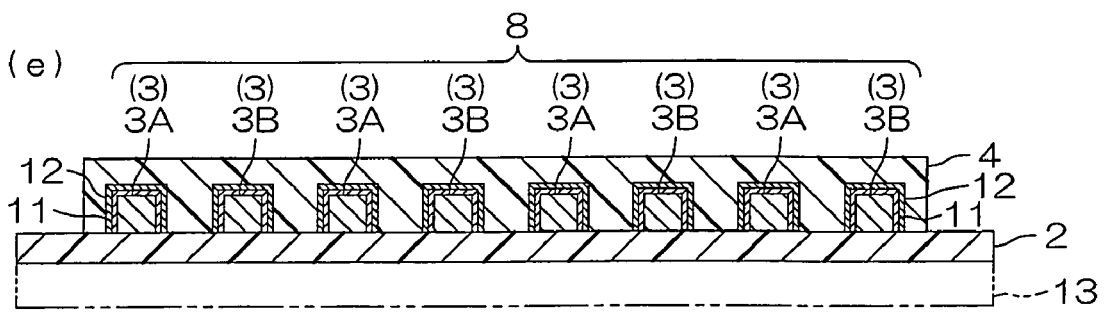

FIG. 3 is a production process view showing a producing method of the gas detection sensor shown in FIG. 2.

Next, the producing method of the gas detection sensor 1 is described with reference to FIG. 3.

In the method, as shown in FIG. 3(a), the insulating layer 2 is prepared first.

As an insulating material for forming the insulating layer 2, any insulating material having flexibility is appropriate. For example, a synthetic resin is used, such as a liquid crystal polymer (LCP such as a polymer of an aromatic or aliphatic dihydroxy compound, a polymer of an aromatic or aliphatic dicarboxylic acid, a polymer of an aromatic hydroxy carboxylic acid, or a polymer of aromatic diamine, aromatic hydroxy amine, or an aromatic aminocarboxylic acid), polyethylene terephthalate (PET), polyimide (PI), polyether nitrile, polyether sulfone, polyethylene naphthalate, polyphenylene sulfide (PPS), polyether imide (PEI), or a polyvinyl chloride. These insulating materials may be used either alone or in combination.

As such an insulating material, a material which is low in water absorption coefficient, humidity expansion coefficient, thermal expansion coefficient, and gas permeability is preferably used.

Preferably, a liquid crystal polymer or polyethylene terephthalate is used. Because of their low water absorption coefficients and gas permeabilities (such as oxygen permeabilities), a liquid crystal polymer or polyethylene terephthalate can prevent the insulating layer 2 from swelling through the absorption of water vapor in an atmosphere, and can prevent a gas or water vapor from permeating from the lower surface of the insulating layer 2, and giving influence to the conductive layer 4. Therefore, it is possible to prevent erroneous detection based on such swelling of the insulating layer 2, and erroneous detection based on the influence of permeation through the insulating layer 2.

To prepare the insulating layer 2, a sheet of the insulating material mentioned above, e.g., is prepared. The insulating layer 2 can also be prepared by forming a varnish of the insulating material into a film on a release plate not shown by casting, drying the film, and then curing it as necessary.

As the sheet of the insulating material mentioned above, a commercially available product can be used. Examples of the commercially available product include a VECSTAR series (a liquid crystal polymer sheet commercially available from KURARAY Co., Ltd.), a BIAC series (a liquid crystal polymer sheet commercially available from Japan Goatex Co., Ltd.), and a Lumirror series (a polyethylene terephthalate commercially available from TORAY Industries, Inc.).

The thickness of the insulating layer 2 thus formed is in a range of, e.g., 5 to 150 μm, or preferably 15 to 75 μm.

Next, in this method, as shown in FIG. 3(b), the conductive pattern 8 is formed on the insulating layer 2.

Examples of a material used to form the conductive pattern 8 include conductive materials such as copper, nickel, gold, tin, rhodium, a solder, and an alloy thereof. Preferably, in terms of conductivity and workability, copper is used.

The conductive pattern 8 is formed as the wired circuit pattern mentioned above by a known patterning method such as, e.g., a printing method, an additive method, or a subtractive method.

In the printing method, e.g., a paste containing fine grains of the material mentioned above is screen-printed in the foregoing pattern on the surface of the insulating layer 2, and then sintered. In this manner, the conductive pattern 8 is formed directly on the surface of the insulating layer 2.

In the additive method, e.g., a conductive thin film (seed film) not shown is formed first on the surface of the insulating layer 2. A chromium thin film and a copper thin film as the conductive thin film are successively laminated by sputtering, or preferably chromium sputtering and copper sputtering.

Next, a plating resist is formed in a pattern reverse to the conductive pattern mentioned above on the surface of the conductive thin film, and then the conductive pattern 8 is formed by electrolytic plating on the surface of the conductive thin film exposed from the plating resist. Thereafter, the plating resist and the conductive thin film at the portion where the plating resist has been laminated are removed.

In the subtractive method, e.g., a two-layer base material (such as a copper-foil two-layer base material) in which a conductive layer made of the conductive material mentioned above is preliminarily laminated on the surface of the insulating layer 2) is prepared first. On the conductive layer, a dry film resist is laminated, exposed to light, and then developed to form an etching resist in the same pattern as the conductive pattern mentioned above. Thereafter, the conductive layer exposed from the etching resist is etched by chemical etching (wet etching), and then the etching resist is removed to form the conductive pattern 8. In the preparation of the two-layer base material, a known adhesive layer can also be interposed between the insulating layer 2 and the conductive layer as necessary.

In the formation of the conductive pattern 8 by the subtractive method described above, a commercially available product can be used as the copper-foil two-layer base material. For example, a copper-clad liquid-crystal-polymer laminated plate (ESPANEX L Series, Single-Sided Product, Standard Type/P Type, commercially available from Nippon Steel Chemical Co., Ltd.) is used in which a conductive layer made of copper is preliminarily laminated on the surface of the insulating layer 2 made of a liquid crystal polymer.

Among these patterning methods, the printing method is preferably used. In accordance with this method, the conductive pattern 8 can be reliably formed directly on the surface of the insulating layer 2. As a result, the detection of a specific gas can be performed with high accuracy.

The thicknesses of the electrodes 3 and the wires 7 thus formed are in a range of, e.g., 3 to 50 μm, or preferably 5 to 20 μm. The lengths of the first electrodes 3A are in a range of, e.g., 5 to 100 mm, or preferably 10 to 50 mm. The lengths of the second electrodes 3B are in a range of, e.g., 5 to 100 mm, or preferably 10 to 50 mm. The lengths of the first electrodes 3A and the lengths of the second electrodes 3B which are covered with the conductive layer 4 are in a range of, e.g., 5 to 100 mm, or preferably 10 to 50 mm. The width (the length in the parallel direction of the electrodes 3) of each of the electrodes 3 and the width (the length in the direction in which the electrodes 3 extend) of each of the wires 7 are in a range of, e.g., 10 to 500 μm, or preferably 20 to 300 μm. The spacing between the first electrode 3A and the second electrode 3B which are adjacent to each other is in a range of, e.g., 20 to 2000 μm, or preferably 100 to 1500 μm. The spacings between the first wires 7A and the second wires 7B are in a range of, e.g., 10 to 150 mm, or preferably 15 to 60 mm.

Next, in this method, as shown in FIG. 3(c), the first protective layer 11 is formed so as to cover the conductive pattern 8.

Examples of a material used to form the first protective layer 11 include a metal material such as tin. Besides, an alloy material such as a tin alloy of tin and copper is used. If the first protective layer 11 is formed as a tin layer or a tin alloy layer, even when a specific gas to be detected is an acidic gas, and a pin hole is formed in the second protective layer 12 described next, the erosion of the conductive pattern 8 can be prevented by the tin layer or the tin alloy layer having an excellent erosion resistant property.

The first protective layer 11 is formed by a known thin-film formation method such as, e.g., sputtering, or plating such as electroless plating or electrolytic plating so as to cover the conductive pattern 8.

The thickness of the first protective layer 11 thus formed is in a range of, e.g., 0.2 to 2 μm, or preferably 0.5 to 1.5 μm.

Next, in this method, as shown in FIG. 3(d), the second protective layer 12 is formed so as to cover the first protective layer 11.

Examples of a material used to form the second protective layer 12 include a metal material such as gold. If the second protective layer 12 is formed as a gold layer, even when the specific gas to be detected is an acidic gas, the erosion of the conductive pattern 8 can be reliably prevented by the gold layer.

The second protective layer 12 is formed by a known thin-film formation method such as, e.g., sputtering, or plating such as electroless plating or electrolytic plating so as to cover the first protective layer 11.

The thickness of the second protective layer 12 thus formed is in a range of, e.g., 0.05 to 3 μm, or preferably 0.5 to 1.5 μm.

Next, in this method, as shown in FIG. 3(e), the conductive layer 4 is formed in the foregoing pattern which covers the conductive pattern 8 on the insulating layer 2.

The conductive layer 4 is formed from a conductive material. The conductive material is a material which swells at a ratio varying in accordance with a type and/or a quantity of the specific gas. For example, the conductive layer 4 is formed from a mixture of a conductive substance and a nonconductive substance.

Examples of the conductive substance which may be used include an organic conductor, an inorganic conductor, or an organic/inorganic conductor mixture.

Examples of the organic conductor which may be used include conductive polymers such as polyanilines, polythiophenes, polypyrroles, polyacetylenes, carbonaceous substances such as carbon blacks, graphites, cokes, and $C_{60}$, and charge-transfer complexes such as tetramethylparaphenylene diamine chloranil, a tetracyanoquinodimethane-alkali metal complex, and a tetrathiofulvalene-halogen complex.

Examples of the inorganic conductor which may be used include metals such as silver, gold, copper, and platinum, alloys of the metals mentioned above such as a gold-copper alloy, highly doped semiconductors such as silicon, gallium arsenide (GaAs), indium phosphide (InP), molybdenum sulfide ($MoS_2$), and titanium oxide ($TiO_2$), conductive metal oxides such as indium oxide ($In_2O_3$), tin oxide ($SnO_2$), and sodium platinum oxide ($Na_xPt_3O_4$), and superconductors such as $YBa_2Cu_3O_7$, and $Tl_2Ba_2Ca_2Cu_3O_{10}$.

Examples of the organic/inorganic conductor mixture which may be include a tetracyano-platinum complex, an iridium-halocarbonyl complex, and a laminated large ring complex.

These conductive substances can be used either alone or in combination.

Examples of the nonconductive substance which may be used include nonconductive organic polymers such as a carbon backbone polymer, an acyclic heteroatom backbone polymer, and a heterocyclic backbone polymer.

Examples of the carbon backbone polymer which may be used include polydienes, polyalkenes, polyacryls, polymethacryls, polyvinylethers, polyvinylthioethers, polyvinylalcohols, polyvinylketones, polyvinylhalides, polyvinylInitriles, polyvinylesters, polystyrenes, poly(α-methylstyrenes), polyarylenes, and polyvinylacetates.

Examples of the acyclic heteroatom backbone polymer include polyoxides, polycarbonates, polyesters, polyanhydrides, polyurethanes, polysulfonates, polysiloxanes, polysulfides, polythioesters, polysulfones, polysulfonamides, polyamides, polyureas, polyphosphazens, polysilanes, and polysilazanes.

Examples of the heterocyclic backbone polymer include poly(furan tetracarboxylic acid diimides), polybenzoxazoles, polyoxadiazoles, polybenzothiazinophenothiazines, polybenzothiazoles, polypyrazinoquinoxalines, polypyromellitoimides (polypiromenitimides), polyquinoxalines, polybenzimidazoles, polyoxindoles, polyoxoisoindolines, polydioxoisoindolines, polytriazines, polypyridazines, polypiperazines, polypyridines, polypiperizines, polytriazoles, polypyrazoles, polypyrrolidines, polycarboranes, polyoxabicyclononanes, polydibenzofurans, polyphthalides, polyacetales, polyvinylpyrrolidones, polybisphenols, and other hydrocarbons.

These nonconductive substances can be used either alone or in combination.

To form the conductive layer 4 mentioned above, a known method such as solution casting, suspension casting, or mechanical mixing is used.

In the solution casting, e.g., a conductive substance and a nonconductive substance (or precursor substances thereof) are blended in a solvent to be dissolved therein, and the obtained solution is coated by a known coating method such as spinning, spraying, or dipping. Thereafter, by evaporating the solvent, the conductive layer 4 can be formed.

As the solvent, any solvent is appropriate as long as the conductive substance and the nonconductive substance (or the precursor substances thereof) can be dissolved therein. For example, a nonaqueous solvent such as tetrahydrofuran (THF), or acetonitrile is used.

To the solution, a known additive such as a catalyst can be added as necessary.

In the suspension casting, a suspension obtained by suspending at least one component of the conductive substance in a dispersion medium, and dissolving the other components therein is coated by the same known coating method as mentioned above. Thereafter, by evaporating the dispersion medium, the conductive layer 4 can be formed.

To the suspension in the suspension casting, the same additive as mentioned above can be added as necessary.

As the dispersion medium, any dispersion medium is appropriate as long as at least one component of the conductive substance, e.g., the conductive substance can be dispersed therein. The same nonaqueous solvent (nonaqueous dispersion medium) as mentioned above, water, or the like is used.

In the preparation of the suspension, the conductive substance is suspended in the dispersion medium with a known agitator such as, e.g., a forcible agitator or an ultrasonic agitator.

In the coating by the solution casting or the suspension casting mentioned above, when the precursor substance of the conductive substance, e.g., is used, the precursor substance (monomer) is caused to react (polymerized) with the coating of the solution (or the suspension) or with the evaporation of the solvent (or the dispersion medium) to generate the conductive substance. More specifically, in the case of using, e.g., pyrrole as the precursor substance, when a solution containing THF, pyrrole, and a phosphomolybdic acid (catalyst) is coated, or when THF is evaporated after the coating, pyrrole is oxidized and polymerized to generate a polypyrrole.

In the preparation of the solution in the solution casting or in the preparation of the suspension in the suspension casting, the mixing ratio of each of the components based on 100 parts by weight of the nonconductive substance is as follows. The mixing ratio of the conductive substance is in a range of, e.g., 10 to 50 parts by weight, or preferably 20 to 35 parts by weight, and the mixing ratio of the solvent or the dispersion medium is in a range of, e.g., 200 to 2000 parts by weight, or preferably 500 to 1000 parts by weight.

In the mechanical mixing, the conductive substance, the nonconductive substance, and the foregoing additive added as necessary are blended, and physically mixed with a known mixer such as a ball mill. In the mechanical mixing, when the nonconductive substance has thermoplasticity, it is also possible to perform efficient mixing, while heating the mixture of the components mentioned above to melt or soften the nonconductive substance.

In the mechanical mixing described above, the mixing ratio of each of the components based on 100 parts by weight of the nonconductive substance is as follows. The mixing ratio of the conductive substance is in a range of, e.g., 10 to 50 parts by weight, or preferably 20 to 35 parts by weight.

To the formed conductive layer 4, conductivity can also be imparted by performing a doping process (e.g., a process of exposure to iodine) as necessary.

In the conductive layer 4 thus formed, an electric path (path) formed by the conductive substance between the first electrodes 3A and the second electrodes 3B becomes an electrical obstacle due to a gap formed by the nonconductive substance. By the gap resulting from the nonconductive substance, a predetermined electric resistance is imparted between the first electrodes 3A and the second electrodes 3B, and the predetermined electric resistance mentioned above changes due to the swelling of the conductive layer 4 based on the absorption or adsorption of the specific gas described later.

The thickness of the conductive layer 4 is in a range of, e.g., 0.01 to 50 μm, preferably 0.1 to 20 μm, or more preferably 0.2 to 10 μm. The size of the conductive layer 4 is selected appropriately in accordance with the shapes of the electrodes 3. For example, the length of the conductive layer 4 in the direction in which the electrodes 3 extend is in a range of 5 to 100 mm, or preferably 10 to 50 mm. The length of the conductive layer 4 in the parallel direction of the electrodes 3 is in a range of 5 to 100 mm, or preferably 10 to 50 mm.

In this manner, the gas detection sensor 1 can be produced. Since the gas detection sensor 1 includes the insulating layer 2 having flexibility, and the conductive pattern 8, it is formed as a flexible wired circuit board.

Thereafter, as shown in FIG. 1, the gas detection sensor 1 is connected to the electric resistance detector 10 via the first wire 7A and the second wire 7B.

Next, a description will be given to a method of detecting the specific gas using the gas detection sensor 1.

First, in this method, the gas detection sensor 1 is disposed at a place where the specific gas is to be detected.

The specific gas detected by the gas detection sensor 1 is not particularly limited. Examples of the specific gas which can be listed include organic substances such as alkane, alkene, alkyne, allene, alcohol, ether, ketone, aldehyde, carbonyl, and carbanion, derivatives (such as, e.g., halogenated derivatives) of the organic substances mentioned above, biochemical molecules such as sugar, isoprene, isoprenoid, chemical substances such as a fatty acid, and a derivative of a fatty acid.

Thereafter, in this method, the electric resistance between the first electrodes 3A and the second electrodes 3B is detected by the electric resistance detector 10. More specifically, when the specific gas comes into contact with the nonconductive substance in the conductive layer (conductive material) 4, the nonconductive substance absorbs or adsorbs the specific gas, and swells in accordance with the type and/or a quantity of the specific gas. Then, the conductive layer 4 also swells to change the electric resistance value of the conductive layer 4 between the first electrodes 3A and the second electrodes 3B. The change in the electric resistance value is detected by the electric resistance detector 10.

The detected change in electric resistance value is analyzed by a computer, not shown, having a predetermined library to effect qualitative analysis and/or quantitative analysis for the type and/or a quantity (concentration) of the specific gas.

Such analysis of the change in electric resistance value can be performed in accordance with the description in Domestic-Phase PCT Patent Application No. 11-503231 or U.S. Pat. No. 5,571,401.

Since the gas detection sensor 1 includes the insulating layer 2 having flexibility, the gas detection sensor 1 can be disposed in a narrow small portion of thin equipment (thin electric equipment) or small-size equipment (small-size electric equipment) by flexibly deforming or compacting the insulating layer 2 through bending, folding, rounding, or the like. It is also possible to dispose the gas detection sensor 1 in the movable portion of the equipment, and allow the gas detection sensor 1 to follow the movement of the equipment.

Therefore, by detecting the electric resistance value of the conductive layer (conductive material) 4 which swells at a ratio varying in accordance with the specific gas using the electric resistance detector 10, the qualitative analysis and quantitative analysis of the specific gas in the narrow small portion or the movable portion can be reliably performed.

The description has been given above using the gas detection sensor 1 as an example of the substance detection sensor of the present invention. However, in the substance detection sensor of the present invention, the state of the substance to be detected is not particularly limited. For example, the specified substance to be detected may also be a liquid.

Figure 4:
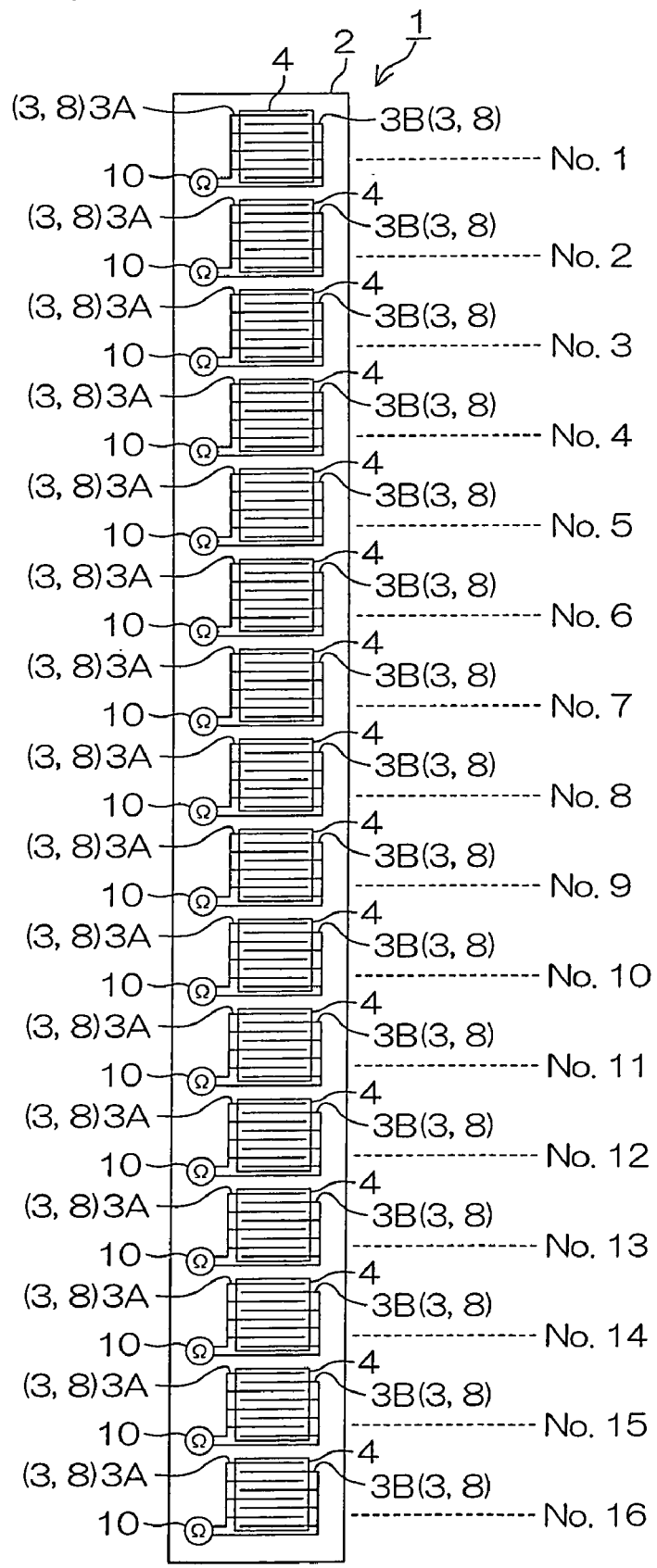
FIG. 4 is a plan view of a gas detection sensor as another embodiment of the substance detection sensor of the present invention.
Figure 5:
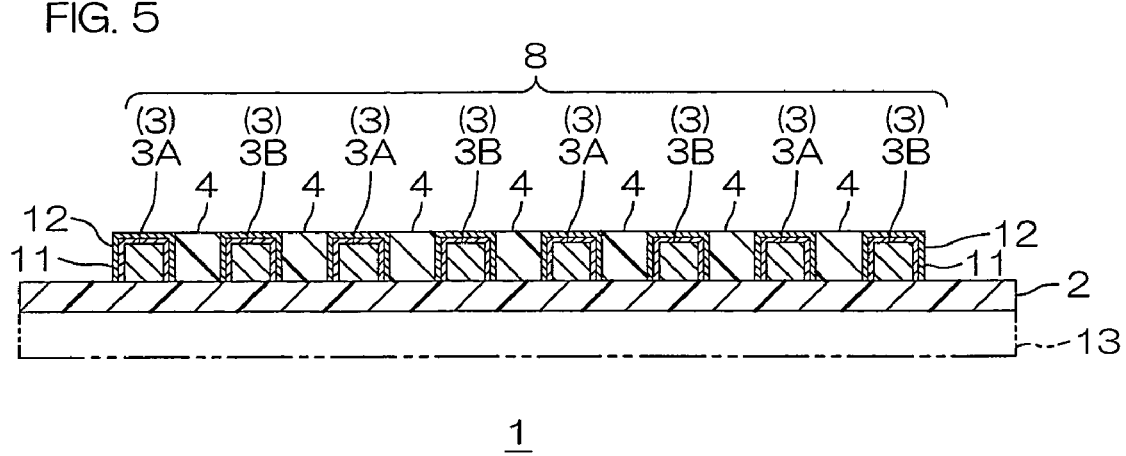
FIG. 5 is a cross-sectional view of the gas detection sensor as the another embodiment of the substance detection sensor of the present invention, which corresponds to FIG. 2.

FIG. 4 is a plan view of the gas detection sensor as another embodiment of the substance detection sensor of the present invention. FIG. 5 is a cross-sectional view of a gas detection sensor as the another embodiment of the substance detection sensor of the present invention, which corresponds to FIG. 2. The members corresponding to the individual components mentioned above are provided with the same reference numerals in FIGS. 4 and 5, and a detailed description thereof is omitted.

In the description given above, the single conductive pattern 8 and the single conductive layer 4 are formed on the single insulating layer 2. However, the numbers of the conductive patterns 8 and the conductive layers 4 are not particularly limited. For example, as shown in FIG. 4, a plurality of (sixteen) conductive patterns 8 can be formed in a row on the single insulating layer 2 to be spaced apart from each other, while a plurality of (sixteen) conductive layers 4 of mutually different types can be formed correspondingly to the respective conductive patterns 8. This can allow detection of gases of different types with the respective conductive patterns 8. In FIG. 4, the plurality of conductive patterns 8 are arranged in a row. However, an arrangement of the plurality of conductive patterns 8 can be freely selected in accordance with the shape of the insulating layer 2, the conductive layer 4, or the electrode 3. For example, the plurality of conductive patterns 8 can also be arranged in four vertical columns and four horizontal rows, or in two vertical columns and eight horizontal rows, though not shown.

By thus providing the gas detection sensor 1, the types of specific gases that can be detected can be increased, and the type and quantity (concentration) of the specific gas can be detected with higher accuracy.

In the description given above, the plurality of (four) first electrodes 3A and the plurality of (four) second electrodes 3B are formed in the formation of the electrodes 3. However, the numbers thereof are not particularly limited. For example, it is also possible to form the single first electrode 3A and the single second electrode 3B.

In the description give above, the lower surface of the insulating layer 2 is exposed. However, as indicated by the imaginary line in FIG. 2, the lower surface of the insulating layer 2 can also be covered with the metal layer 13.

The metal layer 13 is formed under the insulating layer 2. More specifically, the metal layer 13 is provided on the entire lower surface of the insulating layer 2.

Examples of a metal material used to form the metal layer 13 include stainless steel, a 42-alloy, aluminum, a copper-beryllium alloy, and phosphor bronze. Preferably, in terms of an erosion resistant property, stainless steel is used.

To provide the metal layer 13, e.g., the metal layer 13 mentioned above is prepared in advance, and then the insulating layer 2 is formed. Otherwise, the metal layer 13 and the insulating layer 2 can also be prepared as a two-layer base material in which the metal layer 13 and the insulating layer 2 are successively laminated in advance. Otherwise, the metal layer 13 and the insulating layer 2 can also be prepared as a three-layer base material in which the metal layer 13, the insulating layer 2, and the conductive layer (the conductive layer for forming the conductive pattern 8) are successively laminated in advance. As such a three-layer base material, a commercially available product can be used. For example, a copper-clad liquid-crystal-polymer laminated plate (ES-PANEX L Series, Double-Sided Product, Standard Type/P Type, commercially available from Nippon Steel Chemical Co., Ltd.) is used in which the insulating layer 2 made of a liquid crystal polymer and the conductive layer made of copper are laminated in advance on the surface of the metal layer 13 made of copper.

The thickness of the metal layer 13 is in a range of, e.g., 0.05 to 50 μm, or preferably 0.1 to 20 μm. When the thickness of the metal layer 13 exceeds 50 μm, it may be difficult to ensure the flexibility of the gas detection sensor 1. When the thickness of the metal layer 13 is less than 0.05 μm, it may be difficult to prevent permeation of a gas through the insulating layer 2.

When the metal layer 13 is provided under the insulating layer 2, particularly the insulating layer 2 made of an insulating material having a high gas permeability, the metal layer 13 can block a gas which attempts to come in contact with the insulating layer 2 from below. As a result, it is possible to prevent the insulating layer 2 from swelling through the absorption of water vapor in an atmosphere, and prevent a gas or water vapor from permeating from the lower surface of the insulating layer 2, and giving influence to the conductive layer 4. Therefore, it is possible to prevent erroneous detection based on such swelling of the insulating layer 2 and erroneous detection based on the influence of permeation through the insulating layer 2.

In the description given above, the conductive layer 4 is formed so as to cover the surfaces of the electrodes 3, i.e., the individual upper surfaces and side surfaces of the electrodes 3. However, it is sufficient for the conductive layer 4 to be formed so as to come in contact with the first electrodes 3A and the second electrodes 3B. For example, as shown in FIG. 5, the conductive layer 4 can also be formed so as to cover only the individual side surfaces (the individual side surfaces of the second protective layer 12) of the electrodes 3.

In the description given above, the first protective layer 11 and the second protective layer 12 are formed so as to cover the conductive pattern 8. However, it is sufficient for the first protective layer 11 and the second protective layer 12 to cover the electrodes 3. For example, the first protective layer 11 and the second protective layer 12 can be formed so as to cover only the electrodes 3, and not to cover the wires 7, though not shown.

In the description given above, both of the first protective layer 11 and the second protective layer 12 are formed. However, it is also possible to form only either one of the first protective layer 11 and the second protective layer 12, though not shown.

EXAMPLES

Production of Gas Detection Sensor

Example 1

Copper-clad liquid-crystal-polymer laminated plates (Product Number: ESPANEX LC-18-50-00NE, Single-Sided Product, Standard Type, commercially available from Nippon Steel Chemical Co., Ltd.) in each of which a copper foil having a thickness of 18 μm was laminated in advance on a surface of a liquid-crystal polymer sheet having a thickness of 50 μm were prepared, and sixteen conductive patterns were each formed by a subtractive method (see FIGS. 3(b) and 4).

Then, a gold layer having a thickness of 0.5 μm was formed on the surface of each of the conductive patterns (see FIG. 3(d)).

Then, respective solutions having the compositions shown below were prepared, and coated so as to correspond to the sixteen conductive patterns to form sixteen conductive layers (see FIGS. 3(e) and 4).

The numbers (Nos.) 1 to 16 in FIG. 4 are sensor numbers which correspond to the sixteen compositions shown below. Of the sixteen conductive layers, two (the conductive layers corresponding to Sensor Nos. 1 and 2) did not contain a nonconductive substance.

| Sensor No. | Conductive Substance | Nonconductive Substance |
| --- | --- | --- |
| No. 1 | polypyrrole | — |
| No. 2 | polypyrrole | — |
| No. 3 | polypyrrole | polystyrene |
| No. 4 | polypyrrole | polystyrene |
| No. 5 | polypyrrole | polystyrene |
| No. 6 | polypyrrole | poly(α-methylstyrene) |
| No. 7 | polypyrrole | poly(styrene-acrylonitrile) |
| No. 8 | polypyrrole | poly(styrene-maleic anhydride) |
| No. 9 | polypyrrole | poly(styrene-allyl alcohol) |
| No. 10 | polypyrrole | poly(N-vinylpyrrolidone) |
| No. 11 | polypyrrole | poly(4-vinylphenol) |
| No. 12 | polypyrrole | polyvinylbutyral |
| No. 13 | polypyrrole | polyvinylacetate |
| No. 14 | polypyrrole | polybisphenol-A carbonate |
| No. 15 | polypyrrole | polystyrene |
| No. 16 | polypyrrole | polystyrene |

In the preparation of each of the solutions, the solution was prepared by blending a pyrrole-THF solution containing 19 mg (0.29 millimol) of pyrrole and 5.0 ml of THF, and 5.0 ml of a nonconductive substance-THF solution (not containing a nonconductive substance in each of Sensor Nos. 1 and 2) containing 592 mg (0.25 millimol) of a phosphomolybdic acid and 30 mg of the individual nonconductive substance. Then, each of the prepared solutions was coated on an insulating layer by a solution casting method to form sixteen conductive layers each made of a polypyrrole and the individual nonconductive substance in the foregoing pattern.

Thereafter, the remaining phosphomolybdic acid and the unreacted pyrrole were removed with THF, and the surfaces of the conductive layers were cleaned.

Example 2

Copper-clad polyimide laminated plates in each of which a copper foil having a thickness of 18 μm was laminated in advance on a surface of a polyimide sheet having a thickness of 25 μm were prepared, and sixteen conductive patterns were each formed by a subtractive method (see FIGS. 3(b) and 4).

Then, a tin layer having a thickness of 0.1 μm was formed on the surface of each of the conductive patterns by electroless tin plating (see FIG. 3(c)). Subsequently, a gold layer having a thickness of 0.5 μm was formed on the surface of the tin layer by electroless gold plating (see FIG. 3(d)).

Then, by the same method as in EXAMPLE 1, conductive layers were formed, and the surfaces thereof were cleaned (see FIGS. 3(e) and 4)).

Example 3

Two-layer boards on each of which a stainless steel foil having a thickness of 20 μm and a polyimide sheet having a thickness of 25 μm were laminated were prepared (see FIG. 3(a)). Then, by an additive method, sixteen conductive patterns were each formed on the polyimide sheet (see FIGS. 3(b) and 4).

Then, a tin layer having a thickness of 0.1 μm was formed on the surface of each of the conductive patterns by electroless tin plating (see FIG. 3(c)). Subsequently, a gold layer having a thickness of 0.5 μm was formed on the surface of the tin layer by electroless gold plating (see FIG. 3(d)).

Then, by the same method as in EXAMPLE 1, conductive layers were formed, and the surfaces thereof were cleaned (see FIGS. 3(e) and 4)).

Example 4

Polyethylene terephthalate sheets (Product Number: Lumirror X60, Lumirror Series (commercially available from TORAY Industries. Inc.) having a thickness of 50 μm were prepared (see FIG. 3(a)). Then, by a printing method using a copper paste containing copper fine grains, sixteen conductive patterns were formed on the respective polyethylene terephthalate sheets (see FIGS. 3(b) and 4).

Then, a tin layer having a thickness of 0.1 μm was formed on the surface of each of the conductive patterns by electroless tin plating (see FIG. 3(c)). Subsequently, a gold layer having a thickness of 0.5 μm was formed on the surface of the tin layer by electroless gold plating (see FIG. 3(d)).

Then, by the same method as in EXAMPLE 1, conductive layers were formed, and the surfaces thereof were cleaned (see FIGS. 3(e) and 4)).

(Evaluation)

(Gas Detection)

Using gas detection sensors produced according to EXAMPLES 1 to 4, exposure to a gas (vapor) atmosphere containing an ethanol gas at a known concentration was performed, and the detection of the ethanol gas in the atmosphere was performed.

As a result, in all the gas detection sensors of EXAMPLES 1 to 4, the ethanol gas exactly at the known concentration could be detected.

While the illustrative embodiments of the present invention are provided in the above description, such is for illustrative purpose only and it is not to be construed limitative. Modification and variation of the present invention which will be obvious to those skilled in the art is to be covered by the following claims.

INDUSTRIAL APPLICABILITY

The substance detection sensor of the present invention is used to detect a gas or a liquid, or preferably disposed in a narrow small portion or a movable portion and used.

The invention claimed is:

1. A substance detection sensor comprising:
an insulating layer having flexibility;
two electrodes disposed on the insulating layer in mutually spaced-apart and opposing relation, and connected to an electric resistance detector;
a conductive layer formed on the insulating layer so as to span between the two electrodes, and be electrically connected thereto, the conductive layer swelling at a ratio varying in accordance with a type and/or a quantity of a specific substance, and
a protective layer formed to cover the two electrodes,
wherein the protective layer is a tin layer or a tin alloy layer made of tin and copper,
wherein the conductive layer is made of conductive materials including an organic conductor, and
wherein the conductive layer is formed so as to cover the protective layer formed on individual upper surfaces and individual side surfaces of the two electrodes.

2. The substance detection sensor according to claim 1, wherein the substance is gas.

3. The substance detection sensor according to claim 1, wherein the insulating layer is made of a liquid crystal polymer.

4. The substance detection sensor according to claim 1, wherein the insulating layer is made of polyethylene terephthalate.

5. The substance detection sensor according to claim 1, further comprising a metal layer which is formed under the insulating layer.

6. The substance detection sensor according to claim 1, further comprising a gold layer which is formed so as to cover the protective layer.

* * * * *